United States Patent
Walulik et al.

[11] Patent Number: 5,941,879
[45] Date of Patent: Aug. 24, 1999

[54] METHOD AND APPARATUS FOR EXTERNAL FIXATION OF BONES

[75] Inventors: Stephen B. Walulik, Phillipsburg; Kirk J. Bailey, Andover, both of N.J.

[73] Assignee: Electro-Biology, Inc., Parsippany, N.J.

[21] Appl. No.: 08/972,524

[22] Filed: Nov. 18, 1997

[51] Int. Cl.$^6$ ................................................ A61B 17/56
[52] U.S. Cl. ............................ 606/61; 606/54; 606/55; 606/56; 606/62
[58] Field of Search .................. 606/54, 55, 61, 606/56, 62, 57

[56] References Cited

U.S. PATENT DOCUMENTS

| | | | |
|---|---|---|---|
| 4,615,338 | 10/1986 | Ilizarov et al. | 128/92 |
| 4,784,125 | 11/1988 | Monticelli et al. | 128/92 Z |
| 4,895,141 | 1/1990 | Koeneman et al. | 606/54 |
| 4,978,347 | 12/1990 | Ilizarov | 606/54 |
| 4,978,348 | 12/1990 | Ilizarov | 606/57 |
| 5,074,866 | 12/1991 | Sherman et al. | 606/56 |
| 5,095,919 | 3/1992 | Monticelli et al. | 606/56 |
| 5,376,091 | 12/1994 | Hotchkiss et al. | 606/54 |
| 5,380,322 | 1/1995 | van den Brink et al. | 606/57 |
| 5,437,667 | 8/1995 | Papierski et al. | 606/59 |
| 5,486,176 | 1/1996 | Hildebrand et al. | 606/71 |
| 5,620,442 | 4/1997 | Bailey et al. | 606/54 |
| 5,662,650 | 9/1997 | Bailey et al. | 606/59 |
| 5,803,924 | 9/1998 | Oni et al. | 606/54 |

OTHER PUBLICATIONS

Undated brochure describing Of–Garche Limb Lengther, 12 pages.
EBI Medical Systems brochure entitled "Orthofix® Modulsystem", 61 numbered pages (dated Apr. 1993).

*Primary Examiner*—Michael Buiz
*Assistant Examiner*—Tan-Uyen T. Ho
*Attorney, Agent, or Firm*—Harness, Dickey & Pierce P.L.C.

[57] ABSTRACT

An external fixator for adjustably securing a first bone portion in a position relative to a second bone portion. The fixator includes a first clamping assembly for receiving a first bone screw connected to the first bone portion and a second clamping assembly for receiving a second bone screw connected to the second bone portion. The first and second clamping assemblies are interconnected by a connection member. The external fixator also includes a drive unit for controlling angular adjustment of the second clamping assembly relative to the first clamping assembly.

16 Claims, 4 Drawing Sheets

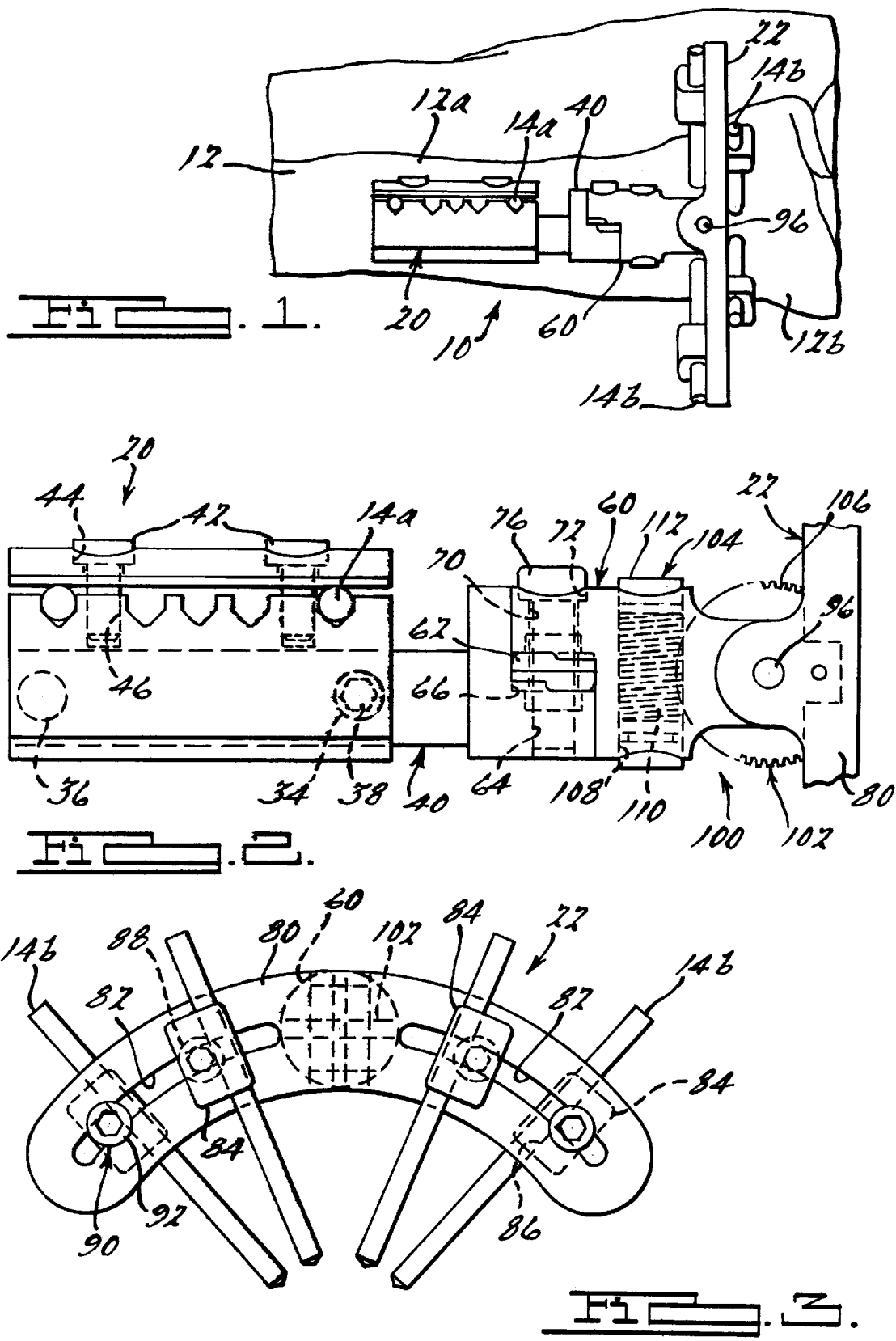

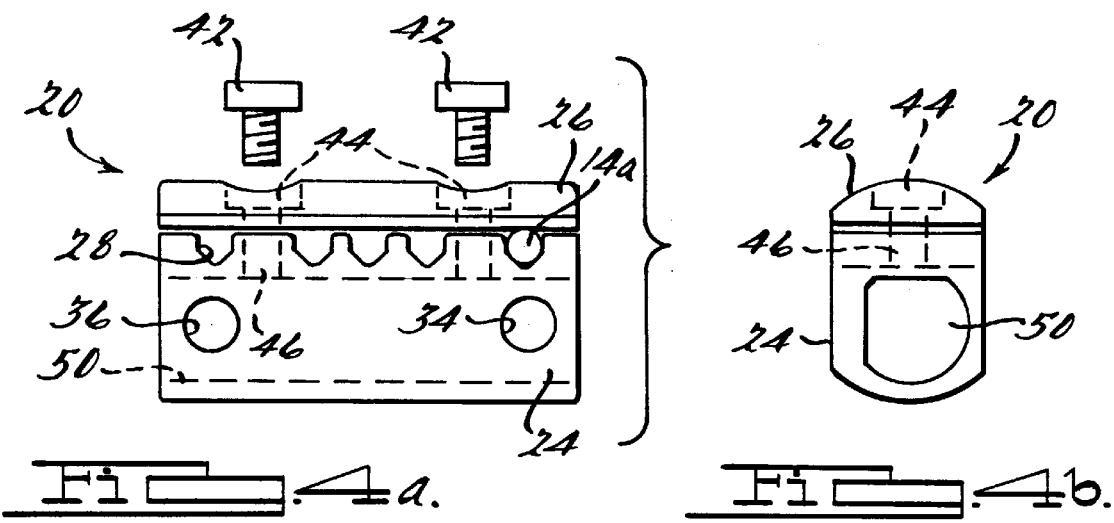
FIG. 4a.
FIG. 4b.
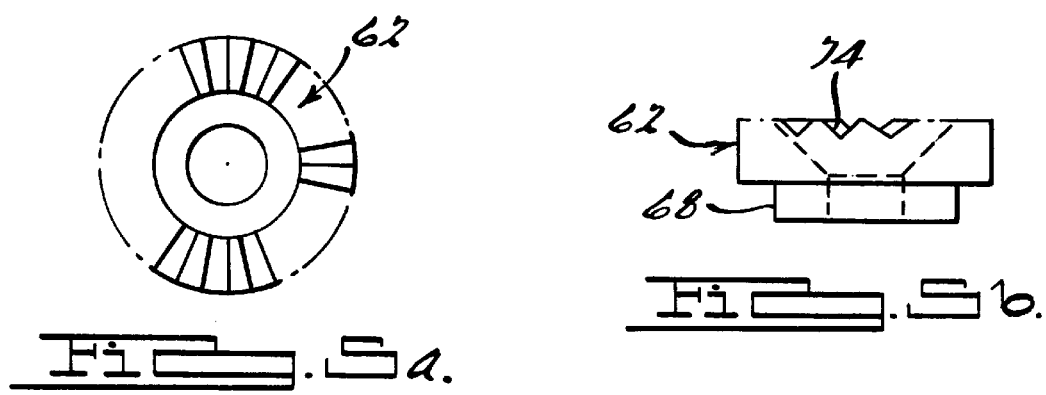
FIG. 5a.
FIG. 5b.
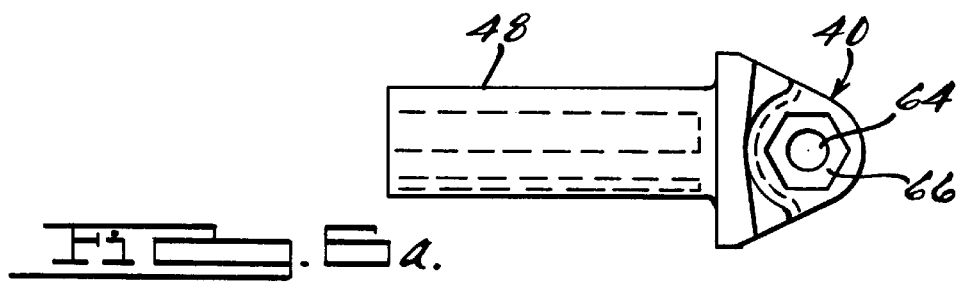
FIG. 6a.
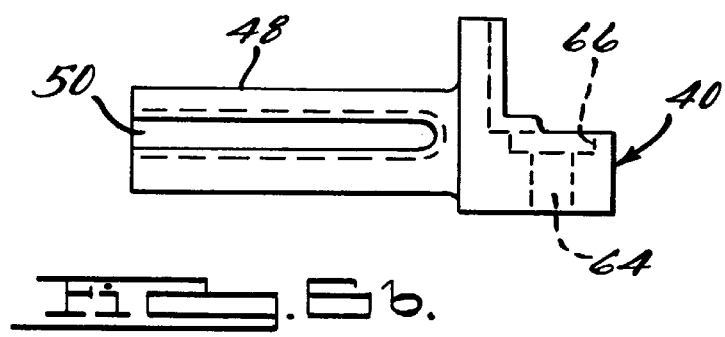
FIG. 6b.

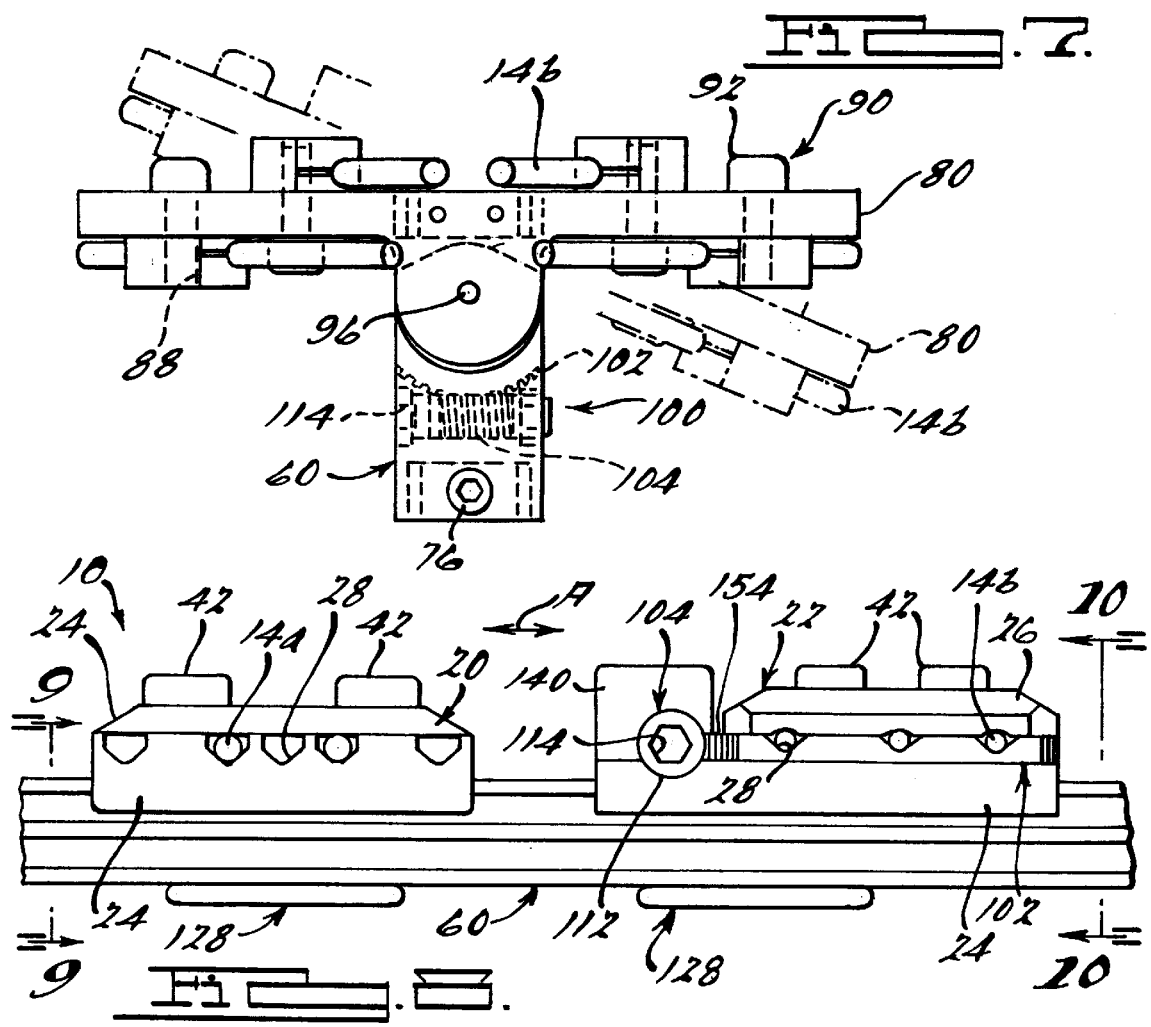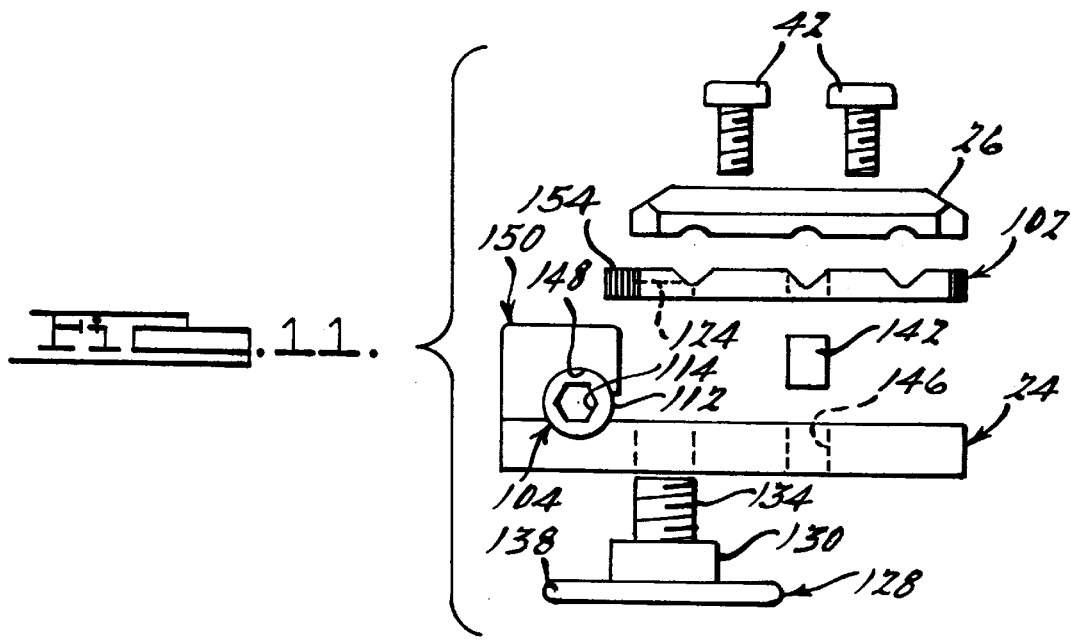

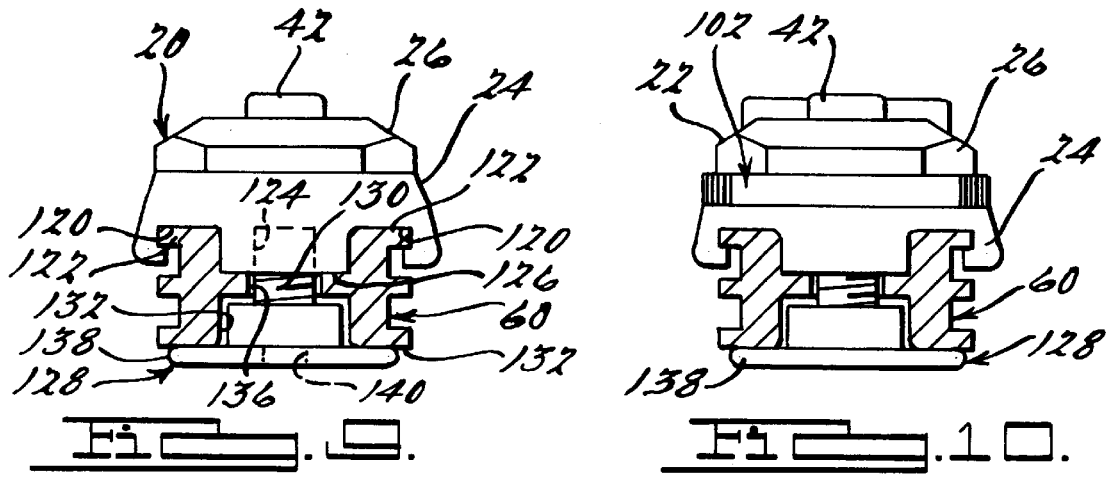
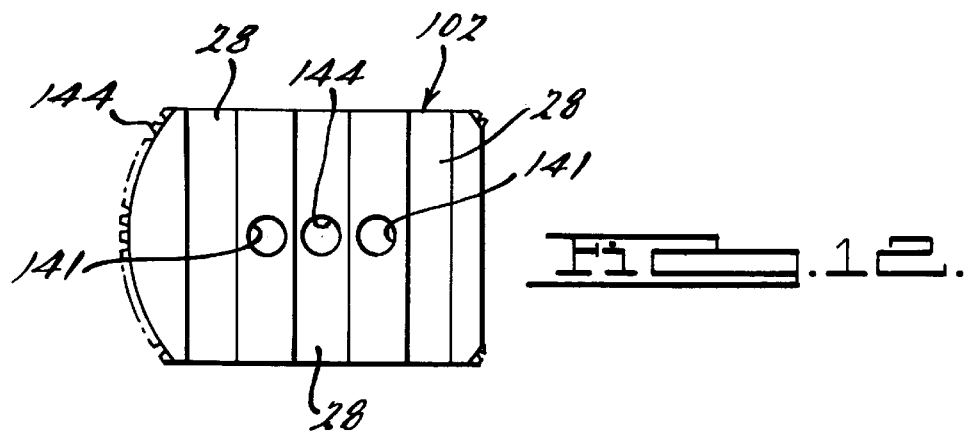
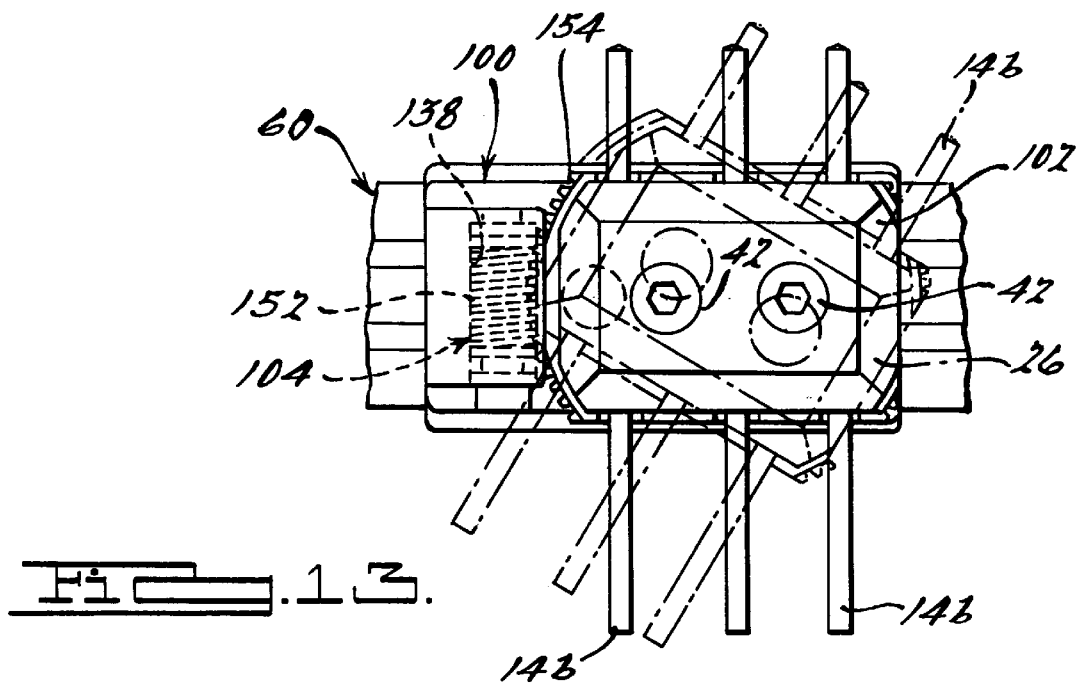

METHOD AND APPARATUS FOR EXTERNAL FIXATION OF BONES

BACKGROUND OF THE INVENTION

1. Field of the Invention

The present invention relates to the external fixation of bones during orthopedic surgical applications, such as the repair of bone fractures and the correction of bone defects. More particularly, the present invention relates to a method and apparatus which allows for gradual angular correction of bone deformities and malunions.

2. Discussion of the Related Art

In various orthopedic surgical procedures, it is necessary to secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be fixed and in the desired position during bone regeneration.

Various external fixation devices for the repair of traumatized bone are known. For example, U.S. Pat. No. 5,662,650 to Bailey et al. discloses an apparatus for the external fixation of large bones. The apparatus is illustrated to include a main body as well as a first and second bone screw clamps. The main body serves to allow the apparatus to axially rotate, thereby providing a proper longitudinal rotational location of the bone screws with respect to a bone. The first bone screw clamp is used to secure a first bone screw to the apparatus while permitting the first bone screw to be axially displaced from the main body. In a similar fashion, the second bone screw clamp which functions to secure a second bone screw to the apparatus and to allow the second bone screw to be axially displaced with respect to the main body. U.S. Pat. No. 5,662,650 is incorporated by reference as if fully set forth herein.

In certain orthopedic surgical procedures, it is necessary to engage two bone portions in a fixed relationship and angularly adjust the two bone portions relative to each other. The need for making such an adjustment is frequently the result of bone deformity. Such bone deformities may result from congenital defects including but not limited to Blount's Disease, Tibia Vara, and Hypophosphatemic Rickets. Angular adjustment of bone portions may also be required as a result of post-traumatic applications, such as the correction of bone malunions.

Other known devices are available for the correction of bone deformities and malunions. For example, the various products manufactured by Orthofix S.r.l. include a fixator having an elongated main body pivotally attached to a T-clamp. The T-clamp attaches to a plurality of bone pins. This fixator further includes a removable compression-distraction unit for angular correction of a bone. The compression-distraction unit attaches to the main body and the T-clamp. Through compression and distraction the unit functions to pivot the T-clamp relative to the main body, and thereby angularly correct the bone.

While the fixators specifically for correcting bone deformities and malunions of the type described above may have proven acceptable for certain applications, such fixators are nevertheless susceptible to improvements that may enhance the performance of the fixator.

SUMMARY OF THE PRESENT INVENTION

In general, the present invention relates to the external fixation of bones. More specifically, the present invention relates to an external fixator which is operable to adjustably secure a first bone portion in a particular position with respect to a second bone portion. The external fixator includes a first means for receiving a bone screw which is secure to the first bone portion and a second means for receiving a second bone screw which is secured to the second bone portion. The external fixator additionally includes a connection member which is operable to connect the first means for receiving the first bone screw with the second means for receiving the second bone screw. The second means for receiving a second bone screw is pivotally attached to the connection member and the external fixator further includes a drive unit for angularly adjusting the first means for receiving the first bone screw and the second means for receiving the second bone screw.

An advantage of the present invention is the provision of a method and apparatus for the external fixation of bone which allows the rate of angular correction of bone deformities and malunions to be easily and more accurately controlled.

Another advantage of the present invention is the provision of a method and apparatus for the external fixation of bone in which an accurate correlation can be made between movement of a drive unit and the degrees of corrective angulation to a bone.

Another advantage of the present invention is the provision of a method and apparatus for the external fixation of bone in which gradual angular corrections can be made to a bone, as opposed to acute angular corrections.

Another advantage of the present invention is the provision of a method and apparatus for angularly correcting a bone which eliminates the nuisance of locking and unlocking a mechanism before angular adjustments can be made.

A more specific advantage of the present invention is the provision of a method and apparatus for the external fixation of bone in which corrective angulation of a bone is obtained through operation of a worm gear.

Additional advantages and features of the present invention will become apparent from the following description and appended claims, taken in conjunction with the accompanying drawings.

BRIEF DESCRIPTION OF THE DRAWINGS

FIG. 1 is an elevational view of an apparatus for the external fixation of bone according to the teachings of a first referred embodiment of the present invention shown in operative association with a human tibia;

FIG. 2 is an enlarged fragmentary view of apparatus for external fixation of bone according to the teachings of the first referred embodiment of the present invention;

FIG. 3 is an end view of the apparatus for the external fixation of bone according to the teachings of the first preferred embodiment of the present invention;

FIGS. 4(a) and 4(b) are illustrations showing the main body of the first clamping assembly shown in FIG. 2. according to the first preferred embodiment of the present invention;

FIGS. 5(a) and 5(b) are illustrations showing one of the grooved locking washers shown in FIG. 2 according to the teachings of the first preferred embodiment of the present invention;

FIGS. 6(a) and 6(b) are illustrations of a rail member of the first clamping assembly shown in FIG. 2 according to the teachings of the first preferred embodiment of the present invention;

FIG. 7 is an elevational view of the apparatus for the external fixation according to the teachings of the first preferred embodiment of the present invention, illustrating a second orientation of the second bone screw clamping assembly in phantom lines;

FIG. 8 is a fragmentary side view of an apparatus for the external fixation of bone according to the teachings of a second preferred embodiment of the present invention;

FIG. 9 is a cross-sectional view taken along the line 9—9 of FIG. 8;

FIG. 10 is a cross-sectional view taken along the line 10—10 of FIG. 8;

FIG. 11 is an exploded view of the second bone screw clamping assembly shown in FIG. 8 according to the teachings of the second preferred embodiment of the present invention;

FIG. 12 is a top view of a driven element shown in FIG. 8 according to the teachings of the second preferred embodiment of the present invention; and FIG. 13 is a fragmentary top view of an apparatus for the external fixation of bone according to the teachings of the second preferred embodiment of the present invention, illustrating a second orientation of the second bone screw clamping assembly in phantom lines.

DETAILED DESCRIPTION OF THE PREFERRED EMBODIMENTS

The following description of the preferred embodiments of the present invention is merely exemplary in nature and is in no way intended to limit the invention or its application or uses.

Referring generally to FIGS. 1–7, an apparatus 10 for the external fixation of a bone 12 is shown. In FIG. 1, the apparatus 10 is shown connected to the bone 12 through a plurality of bone screws 14a and 14b which serve to secure a first bone portion 12a relative to a second bone portion 12b. In the exemplary application illustrated, the first and second bone portions 12a and 12b secured by the apparatus 10 are of a single bone 12. The bone 12 shown in the drawings represents a human tibia. It is to be understood, however, that the apparatus 10 may be operatively attached to a variety of other types of bones and used to correct bone deformities, corrected malunions, or repair fractures. As will become apparent below, by securing the first and second bone portions 12a and 12b with the apparatus 10 of the present invention, the orientation of the first portion 12a relative to the second portion 12b may be angularly adjusted.

The apparatus 10 comprises a first bone screw clamping assembly 20 and a second bone screw clamping assembly 22. The first bone screw clamping assembly 20 is used to secure a first bone screw 14a to the apparatus 10 while permitting the first bone screw 14a to be axially displaced from the second bone screw 14b. The first bone screw clamping assembly 20 includes a main body having a base portion 24 and a cover portion 26. The base portion 24 serves to receive the first bone screw 14a in one of a plurality of grooves 28, while the cover portion 26 serves to secure the first bone screw 14a within the groove 28.

As discussed in detail in U.S. Pat. No. 5,662,650, the grooves 28 include two contact surfaces which are substantially planar so as to permit line contact of the first bone screw 14a in two positions within the grooves 28. Since the first bone screw 14a also engages the cover portion 26 of the first bone screw clamping assembly 20, the first bone screw 14a engages the first bone screw clamping assembly 20 in three positions (i.e., along the contact surfaces of the grooves 28 as well as on the cover portion 26). This provides line contact for the bone screw 14 which secures the bone screws 14 in a more effective manner than if the grooves 28 were cylindrical.

The base portion 24 of the bone screw clamping assembly 20 further includes a first aperture 34 and a second aperture 36. The first aperture 34 is used to receive a threaded fastener 38 (shown in phantom in FIG. 2) which serves to secure a rail member 40 in a locked position as will be more fully discussed below. The second aperture 36 is also used to receive a threaded member (not shown) which is able to secure a compression/distraction member (not shown). One suitable compression/distraction member is described in connection with the external fixator disclosed in U.S. Pat. No. 5,662,650.

The cover portion 26 of the first bone screw clamping assembly 20 is secured to the base portion 24 of the first bone screw clamping assembly 20 by means of two screws 42. To accommodate these screws 42, the cover portion 26 of the bone screw clamping assembly 20 includes two apertures 44 (shown in phantom in FIGS. 2 and 4a) which mate with corresponding apertures 46 in the base portion 24 of the bone screw clamping assembly 20. Accordingly, upon secured threaded engagement of the screws 42 within the apertures 44 and 46, the cover portion 26 of the bone screw clamping assembly 20 may be secured to the base portion 24 of the bone screw clamping assembly 20.

To provide means for laterally displacing the first bone screw clamping assembly 20 with respect to the second bone screw clamping assembly 22, the bone screw clamping assembly 20 further includes a first rail member 40. The rail member 40 includes a D-shaped extension 48 which is able to be received in a D-shaped bore 50 of the bone screw clamping assembly 20. The D-shaped extension 48 includes an elongated slot 51 for receiving the fastener 38. Because of the cross-sectional shape of the D-shaped extension 48, the base portion 24 of the bone screw clamping assembly 20 is able to slide on the extension 48 of the rail member 40. However, the base portion 24 is unable to rotate with respect to the D-shaped extension 48.

To provide means for interconnecting the first and second bone screw clamping assemblies 20 and 22, the apparatus 10 is illustrated to include a connection member 60. The connection member 60 serves to secure the first and second bone screw clamping assemblies 20 and 22. In this regard, a plurality of grooved locking washers 62 are disposed between the rail member 40 and the connection member 60. In particular, the rail member 40 has an aperture 64 with a hex-shaped recess 66 for receiving the base portion 68 of the washer 62. In a similar fashion, the connection member 60 also includes an aperture 70 (shown in phantom in FIG. 2) with a hex-shaped recess 72 (shown in phantom in FIG. 2) for receiving the base portion 68 of the washer 62. Because a groove surface 74 of each of the washers 62 engage each other, the connector member 60 is secured to the first bone clamping assembly 20 upon secured threaded engagement of a screw 76.

The second bone screw clamping assembly 22 is operable to secure a second bone screw 14b to the apparatus 10. As illustrated in the drawings, the second bone screw clamping assembly 22 is preferably operable to secure a plurality of bone screws 14b to the apparatus 10. In this regard, the second bone screw clamping assembly 22 includes a main body 80. The main body 80 is shown to be preferably arcuate in shape and defines a pair of arcuate recesses 82 passing therethrough. The arcuate recesses are operable for adjustably securing the bone screws 14b to the main body 80. In this regard, each of the bone screws 14b is held adjacent to the main body 80 with a retainer member 84. Each of the retainer members 84 defines a channel 86 for receiving one of the bone screws 14b. Each retainer member 84 is further formed to include an internally threaded aperture 88 for receiving a fastener 90. The fastener 90 passes through one of the arcuate slots 82 and includes a head 92 which can be tightened against the opposite side of the main body 80. The arcuate configuration of the main body 80 allows the bone screws 14b of the plurality of the bone screws to converge upon the second portion 12b of the bone 12.

To provide means for angularly adjusting the second clamping assembly 22 relative to the first clamping assembly 20, the second clamping assembly 22 is shown to be pivotally attached to the connection member 60 through a pivot pin 96. The pivot pin 96 defines a pivot axis which is substantially perpendicular to the pivot axis defined by the screw 76 which interconnects the connection member 60 and the first bone screw clamping assembly 20. As shown specifically in FIG. 7, pivotal attachment of the second bone screw clamping assembly 22 and the connection member 60 permit the second bone screw clamping assembly 22 to rotate from a neutral position (shown in solid lines), clockwise (shown in phantom lines), or counterclockwise (not shown) through approximately 30°. The connection member 60 thus permits approximately 60° of relative rotation between the first and second bone screw clamping assemblies 20 and 22.

To provide means for controlling angular displacement of the second bone screw clamping assembly 22 with respect to the first bone screw clamping assembly 20, the apparatus 10 is illustrated to include a drive unit 100. The drive unit 100 is effectively a worm gear assembly including a driven element 102 and a drive element 104. The driven element 102 is fixedly secured to the second bone screw clamping assembly 22 and includes an arcuate perimeter having a plurality of teeth 106. The drive element 104 is rotatably retained within a transversely extending aperture 108 provided in the connection member 60 and includes a plurality of threads 110 operatively engage with the teeth 106 of the driven element 102. The drive element 104 includes a head 112 having a hexagonal recess 114 (shown in phantom in FIG. 7) for receiving an hex wrench or similar tool for rotating the drive element 104. The drive element 104 is rotatable about an axis substantially perpendicular to the pivot axis 96.

Referring again to FIG. 7, when the drive element 104 is rotated in a first direction, the driven element 102 rotates, for example, clockwise. Similarly, when the drive element 104 is rotated in a second direction, the driven element 102 is rotated counterclockwise, thereby angularly adjusting the second bone screw clamping assembly 22 and the bone screws 14b relative to the first bone screw clamping assembly 20 and the first bone screw 14a. The drive unit 100 permits concise correlation between the number of rotations of the drive member 102 and the degrees of corrective angulation of the second bone screw clamping assembly 22. In addition, the nature of the drive unit 100 eliminates the need for a locking mechanism. Therefore, gradual angulation over an extended period of time can be obtained without the nuisance of locking and unlocking a locking bolt.

The second preferred embodiment of the present invention is shown in FIGS. 8–13. In this embodiment, similar reference numerals will be used to identify similar components as previously described with respect to the first preferred embodiment of the present invention. As with the first preferred embodiment of the present invention, the apparatus 10 of the second embodiment of the present invention includes a first bone screw clamping assembly 20 and a second bone screw clamping assembly 22. In the second preferred embodiment, the apparatus 10 includes a longitudinally extending connection member 60 for interconnecting the first and second bone screw clamping assemblies 20 and 22.

As with the first preferred embodiment, the first and second bone screw clamping assemblies 20 and 22 of the second preferred embodiment are operative to secure first and second bone screws 14a and 14b, respectively, to the apparatus 10. The first bone screw clamping assembly 20 of the second preferred embodiment includes a cover 26 attached to a base 24 with a pair of threaded fasteners 42. The cover 26 and the base 24 cooperates to define a plurality of openings 28 for receiving one or more bone screws 14a. In the second preferred embodiment, the first and second bone screws 14a and 14b lie in a common plane. As will become apparent, both of the first and second bone screw clamping assemblies 20 and 22 are adjustable along the connection member 60 in an axial or longitudinal direction indicated by double arrow A in FIG. 8.

With specific reference to the cross-sectional view of FIG. 9, the base portion 24 of the first bone screw clamping assembly 20 of the second preferred embodiment is formed to define a pair of axially extending channels 120. The channels 120 are adapted to slidably retain a pair of outwardly extending flanges 122 integrally formed with an upper surface of the connection member 60. The base portion 24 is further formed to include an internally threaded aperture 124 (shown in phantom lines in FIG. 9) upwardly extending from a bottom side 126. The aperture 124 is operable for receiving a fastener 128 as shown. The fastener 128 includes a head 130 located within an axially extending channel 132 defined by the connection member 60 and a threaded shaft 134 which upwardly extends through an elongated slot 136 and engages the aperture 124.

The threaded fastener 128 further includes a mounting flange 138 operable to abut a lower surface 132 of the connection member 60. The mounting flange 138 defines a hexagonal recess 140 (shown in phantom in FIG. 9) for receiving a hex wrench or similar tool. When the fastener 128 is tightened, the base portion 24 of the first bone screw clamping assembly 20 is drawn against the connection member 60 and axially locked in place.

The second bone screw clamping assembly 22 is similarly constructed to the first bone screw clamping assembly 20. Generally in this regard, the second bone screw clamping assembly 22 is shown to include a base portion 24 and a cover portion 26. As with the first bone screw clamping assembly 20, the base portion 26 is adapted to axially translate relative to the connection member 60 in an identical manner.

To provide means for controlling angular displacement of the second bone screw clamping assembly 22 with respect to the first bone screw clamping assembly 20, the apparatus 10 of the second preferred embodiment includes a drive unit 100. The drive unit 100 includes a driven element 102 which is fixedly secured to the cover 26 of the second bone screw clamping assembly 22. In the exemplary embodiment illustrated, the driven element 102 is a plate interdisposed between the cover 26 and the base 24. The plate 102 is formed to include a pair of apertures 141 for receiving the fasteners 42. The plate 102 is further formed to include a plurality of grooves 28 for receiving the second bone screws 14b. The cover portion 26 cooperates with the grooves 28 to maintain the bone screws 14b.

The plate 102 is pivotally interconnected to the base 24 through a pin 142. The pin 142 engages an aperture 144 in the plate and an aperture 146 in the base portion 24. The plate 102 serves to define a pivot axis.

The drive element 104 is rotatably retained within a transversely extending aperture 148 provided in an upwardly extending rectangular portion 150 which is integrally formed with the base 24. The drive element 104 includes a plurality of threads 152 operatively engaged with a plurality of teeth 154 formed on an arcuate perimeter of the driven member 102. The drive element 104 includes a head 112 having a hexagonal recess 114 for receiving a hex wrench or other similar tool for rotating the drive element 104. The drive element 104 is rotatably about an axis substantially perpendicular to the pivot axis defined by the pin 142.

With specific reference to FIG. 13, when the drive element 104 is rotated in a first direction, the driven element 102 rotates, for example, clockwise. Similarly, when the drive element 104 is rotated in a second direction, the driven element 102 is rotated counterclockwise. As a result of selective rotation of the driven element 102 about the pin 142, the bone screw 14a of the first bone screw clamping assembly 20 is angularly adjusted relative to the bone screw 14b of the second bone screw clamping assembly 22.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claim is:

1. An apparatus for adjustably securing a first bone portion in a fixed relationship to a second bone portion, the apparatus comprising:

a first bone screw operable to be connected to the first bone portion;

a second bone screw operable to be connected to the second bone portion;

means for receiving said first bone screw;

means for receiving said second bone screw;

means for interconnecting said means for receiving said first bone screw and said means for receiving said second bone screw; and means for angularly adjusting said means for receiving said second bone screw relative to said means for receiving said first bone screw, said means for angularly adjusting including a rotatable element fixedly attached to said means for receiving said second bone screw, said rotatable element rotatable about a pivot axis such that rotation of said rotatable element through a predetermined angle causes corresponding angular adjustment of said means for receiving said second bone screw, and a drive element engaging said rotatable element and operable to selectively rotate said rotatable element about said pivot axis; and wherein said rotatable element includes an arcuate perimeter formed to include a plurality of teeth, and further wherein said drive element includes a plurality of external threads in meshing engagement with said plurality of teeth.

2. The apparatus for adjustably securing a first bone portion in a fixed relationship to a second bone portion of claim 1, wherein said drive element is rotatable about an axis substantially perpendicular to said pivot axis.

3. The apparatus for adjustably securing a first bone portion in a fixed relationship to a second bone portion of claim 1, wherein said means for securing said first bone screw is longitudinally translatable relative to said connection member.

4. The apparatus for adjustably securing a first bone portion in a fixed relationship to a second bone portion of claim 3, wherein said means for securing said second bone screw is longitudinally translatable relative to said connection member.

5. An apparatus for adjustably securing a first bone portion in a fixed relationship to a second bone portion, the apparatus comprising:

a first bone screw operable to be connected to the first bone portion;

a second bone screw operable to be connected to the second bone portion;

a first clamping assembly for clamping said first bone screw;

a second clamping assembly for clamping said second bone screw;

a connection member for interconnecting said first clamping assembly to said second clamping assembly;

a drive unit for angularly adjusting said second clamping assembly relative to said first clamping assembly, said drive unit including a rotatable element fixedly attached to said second clamping assembly for rotation about a pivot axis;

wherein said drive unit further includes a drive element engaging said rotatable element and operable to selectively rotate said rotatable element about said pivot axis; and wherein said rotatable element includes an arcuate perimeter formed to include a plurality of teeth, and further wherein said drive element includes a plurality of external threads in meshing engagement with said plurality of teeth.

6. The apparatus for adjustably securing a first bone portion in a fixed relationship to a second bone portion of claim 5, wherein rotation of said rotatably element through a predetermined angle causes corresponding angular adjustment of said second clamping assembly relative to said first clamping assembly.

7. The apparatus for adjustably securing a first bone portion in a fixed relationship to a second bone portion of claim 5, wherein said drive element is rotatable about an axis substantially perpendicular to said pivot axis.

8. The apparatus for adjustably securing a first bone portion in a fixed relationship to a second bone portion of claim 5, wherein said first bone screw is longitudinally translatable relative to said connection member.

9. The apparatus for adjustably securing a first bone portion in a fixed relationship to a second bone portion of claim 5, wherein said second bone screw is longitudinally translatable relative to said connection member.

10. An apparatus for adjustably securing a first bone portion in a fixed relationship to a second bone portion, the apparatus comprising:

at least one bone screw operable to be connected to the first bone portion;

a plurality of bone screws operable to be connected to the second bone portion;

a first clamping assembly for receiving the at least one bone screw;

a second clamping assembly for receiving the plurality of bone screws; and a connection member for interconnecting said first and second clamping assemblies;

said first clamping assembly pivotally attached to the connection member for rotation about a first pivot axis;

said second clamping assembly pivotally attached to said connection member for rotation about a second pivot axis;

a drive unit for angularly adjusting said first clamping assembly relative to said second clamping assembly;

wherein said drive unit includes a rotatable element fixedly attached to said second clamping assembly and a drive element carried by said connection member, said drive element being engaged with said rotatable element and operable for selectively rotating said rotatable element; and wherein said rotatable element includes an arcuate perimeter formed to include a plurality of teeth, and further wherein said drive element includes a plurality of external threads in meshing engagement with said plurality of teeth.

11. The apparatus for adjustably securing a first bone portion in a fixed relationship to a second bone portion of claim 10, wherein said first pivot axis is substantially perpendicular to said second pivot axis.

12. The apparatus for adjustably securing a first bone portion in a fixed relationship to a second bone portion of claim 10, wherein said second clamping assembly includes an arcuate main body portion.

13. The apparatus for adjustably securing a first bone portion in a fixed relationship to a second bone portion of claim 10, wherein said at least one bone screw operable to be connected to said first clamping assembly is longitudinally translatable relative to said plurality of bone screws operable to be connected to said second clamping assembly.

14. An apparatus for adjustably securing a first bone portion in a fixed relationship to a second bone portion, the apparatus comprising:

a first plurality of bone screws operable to be connected to the first bone portion, said first plurality of bone screws being substantially within a plane;

a second plurality of bone screws operable to be connected to the second bone portion, said second plurality of screws being substantially within said plane;

a first clamping assembly for receiving the first plurality of bone screws;

a second clamping assembly for receiving the second plurality of bone screws;

a main body for interconnecting said first and second clamping assemblies, said second plurality of bone screws being pivotally interconnected to said main body for rotation about a pivot axis; and a drive unit for angularly adjusting said first clamping assembly relative to said second clamping assembly;

wherein said main body comprises a longitudinally extending rail, said first and second clamping assemblies attached to said longitudinally extending rail for longitudinal translation along said rail;

wherein said first clamping assembly includes a base member and a cover member, and further wherein said drive unit includes a driven member fixedly attached to said cover and interconnected to said base for rotation about said pivot axis; and wherein said driven member comprises a plate having a perimeter with and arcuate portion formed to include a plurality of teeth.

15. The apparatus for adjustably securing a first bone portion in a fixed relationship to a second bone portion of claim 14, wherein said drive unit further includes a drive member interconnected to said base member for rotation about an axis substantially perpendicular to said pivot axis, said drive member including a plurality of threads in engagement with said plurality of teeth.

16. The apparatus for adjustably securing a first bone portion in a fixed relationship to a second bone portion of claim 14, wherein said cover member and said driven member cooperate to define a plurality of grooves for receiving said first plurality of bone screws.

* * * * *

UNITED STATES PATENT AND TRADEMARK OFFICE
CERTIFICATE OF CORRECTION

PATENT NO. : 5,941,879
DATED : August 24, 1999
INVENTOR(S) : Stephen B. Walulik

It is certified that error appears in the above-identified patent and that said Letters Patent is hereby corrected as shown below:

Title page,
Item [56], Reference Cited, OTHER PUBLICATIONS,
"Orthofix®" should be -- ORTHOFIX® --.

Column 1,
Line 26, delete "a".
Line 33, delete "which".
Line 37, delete "if" and substitute -- is -- therefor.

Column 2,
Line 5, delete "secure" and substitute -- secured -- therefor.
Lines 47 and 51, "referred" should be -- preferred --.
Line 57, delete the period after "FIG. 2."

Column 5,
Line 42, after "110" insert -- to --.
Line 45, delete "an" and substitute -- a -- therefor.

Column 6,
Line 17, delete "cooperates" and substitute -- cooperate --.

Column 7,
Line 18, delete "rotatably" and substitute -- rotatable --.

Column 8,
Line 43, delete "rotatably" and substitute -- rotatable -- therefor.

Signed and Sealed this

Thirtieth Day of April, 2002

Attest:

*Attesting Officer*

JAMES E. ROGAN
*Director of the United States Patent and Trademark Office*